(12) United States Patent
Boyd et al.

(10) Patent No.: US 6,666,068 B2
(45) Date of Patent: Dec. 23, 2003

(54) VAPOR TRAP SYSTEM AND ASSOCIATED METHOD FOR DETECTING VOLATILE ORGANIC CHEMICAL VAPORS

(75) Inventors: Mark Kevin Boyd, Richardson, TX (US); Yale Lynn Clark, Dallas, TX (US)

(73) Assignee: PERTECT Detectors, Inc., Farmers Branch, TX (US)

( * ) Notice: Subject to any disclaimer, the term of this patent is extended or adjusted under 35 U.S.C. 154(b) by 66 days.

(21) Appl. No.: 09/962,950

(22) Filed: Sep. 25, 2001

(65) Prior Publication Data

US 2003/0097889 A1 May 29, 2003

(51) Int. Cl.[7] .......................... G01N 1/24; G01N 33/24
(52) U.S. Cl. ................. 73/31.07; 73/863.21; 73/864.34
(58) Field of Search .......................... 73/31.07, 863.21, 73/864.34, 863.71; 175/58; 324/464; 250/389

(56) References Cited

U.S. PATENT DOCUMENTS

| | | | |
|---|---|---|---|
| 4,111,034 A | | 9/1978 | Hübner |
| 4,155,247 A | * | 5/1979 | Kaczmarek et al. . 73/863.21 X |
| 4,573,354 A | * | 3/1986 | Voorhees et al. ..... 73/863.21 X |
| 4,699,570 A | | 10/1987 | Bohn ........................... 417/6 |
| 4,935,196 A | * | 6/1990 | Griesbach et al. ... 73/863.21 X |
| 5,099,437 A | | 3/1992 | Weber |
| 5,106,232 A | * | 4/1992 | Metzer et al. ............... 405/128 |
| 5,355,739 A | * | 10/1994 | Cooper et al. ....... 73/864.34 X |
| 5,397,552 A | * | 3/1995 | Weigold et al. .......... 422/186.3 |
| 5,481,927 A | * | 1/1996 | Hubbell et al. .......... 73/863.71 |
| 5,563,335 A | | 10/1996 | Howard ............... 73/863.33 X |
| 6,225,633 B1 | | 5/2001 | Sun et al. .................... 250/389 |
| 6,477,907 B1 | * | 11/2002 | Chambers et al. ... 73/863.21 X |
| 2001/0035057 A1 | * | 11/2001 | Jackson et al. ...... 73/863.71 X |

FOREIGN PATENT DOCUMENTS

| | | | | |
|---|---|---|---|---|
| JP | 2000-55908 | * | 2/2000 | ............ G01N/1/24 |
| JP | 2001-289751 | * | 10/2001 | ............ G01N/1/24 |

* cited by examiner

*Primary Examiner*—Thomas P. Noland
(74) *Attorney, Agent, or Firm*—Dennis J. M. Donahue, III; Husch & Eppenberger, LLC

(57) ABSTRACT

A vapor trap for detecting VOCs includes a housing, having a first end portion, a second end portion and at least one opening for receiving gas vapor. The housing is at least partially buried in ground with a vapor containment mechanism detachably connected to the first end portion of the housing. The vapor containment mechanism can be removed after a predetermined time period and replaced with a vapor sampling mechanism. An organic vapor analyzer can be connected in fluid relationship to the vapor sampling mechanism to measure VOCs. Optionally, a vacuum pump can be utilized to draw vapor into the vapor trap and then subsequently into the organic vapor analyzer. There can be a first selector valve located between the vapor sampling mechanism and the vacuum pump and a second selector valve located between the vapor sampling mechanism and the organic vapor analyzer. A preferred organic vapor analyzer is a photo-ionization detector. The method for detecting VOCs utilizing a vapor trap includes at least partially burying a housing in ground that includes a first end portion, a second end portion and at least one opening and sealing the housing with a vapor containment mechanism, e.g., plug. After a predetermined time period, the vapor containment mechanism is removed and replaced with a vapor sampling mechanism. The housing is buried in vapor transmissive material and applied with sealing material to the top portion of the housing to position the housing in a predetermined location. The vapor sampling mechanism is connected in fluid relationship with an organic vapor analyzer with an optional vacuum pump for drawing additional vapors from the housing into the organic vapor analyzer.

25 Claims, 5 Drawing Sheets

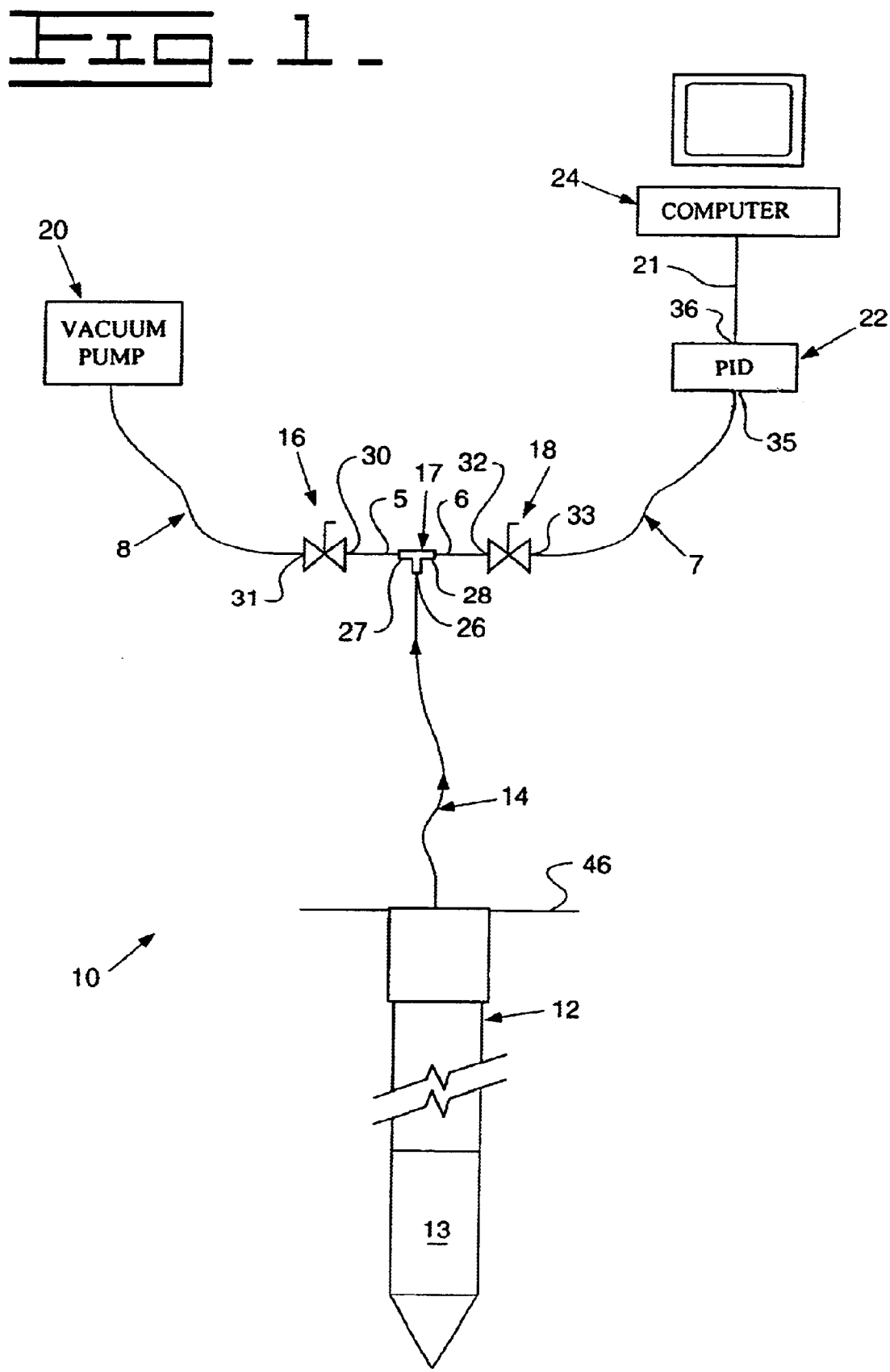

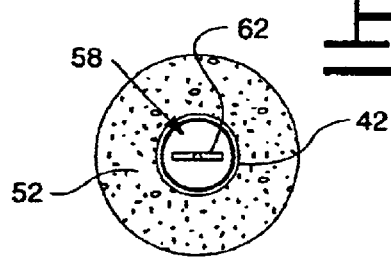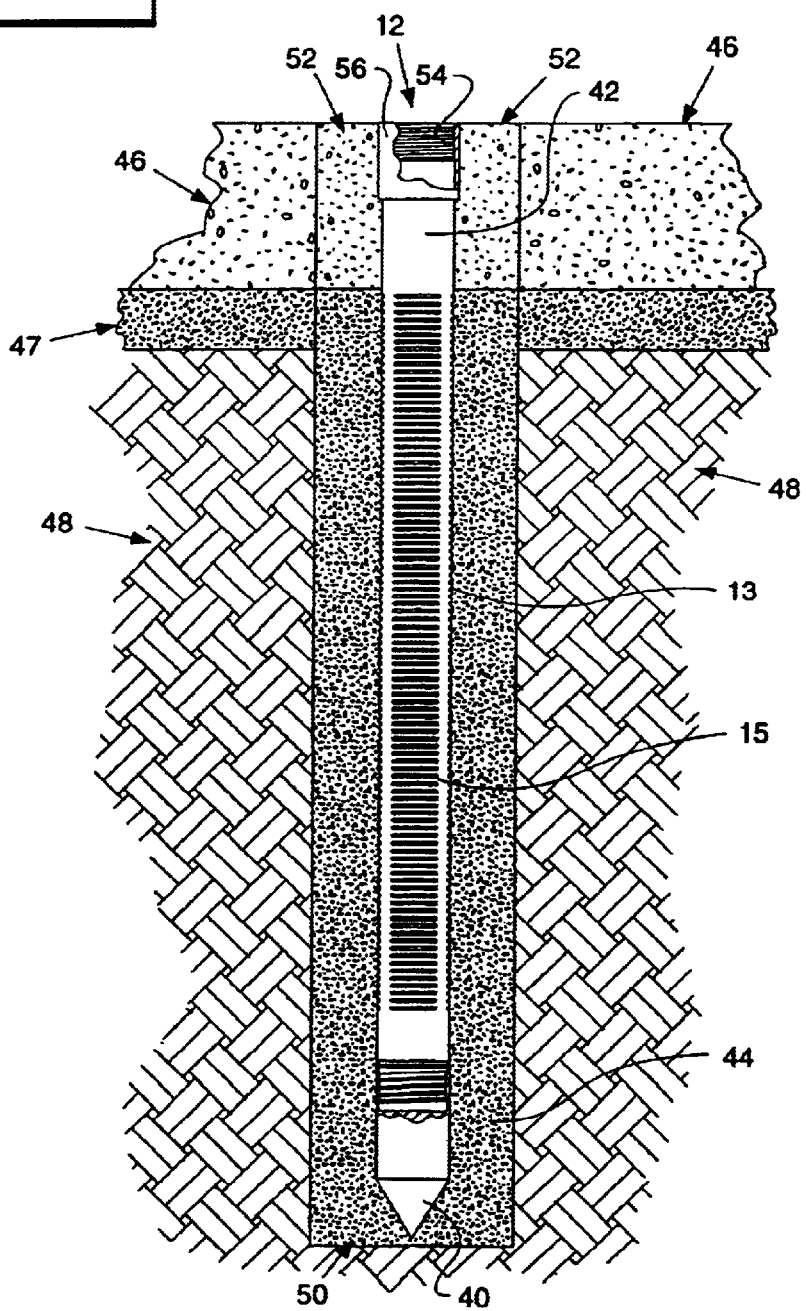

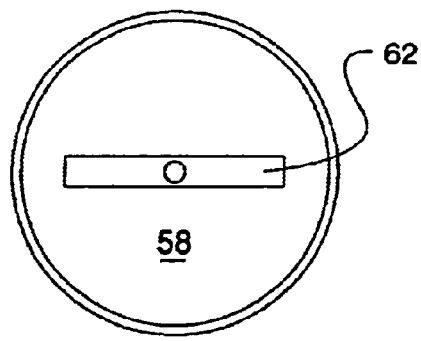
Fig_6_
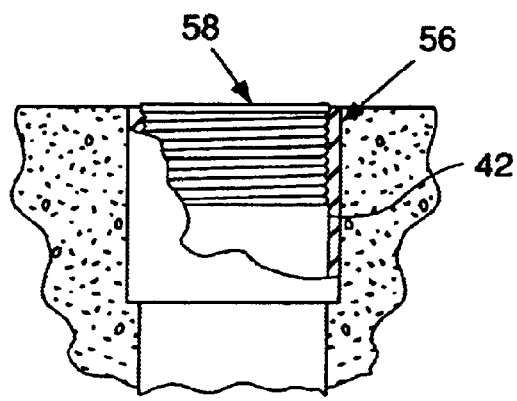
Fig_7_
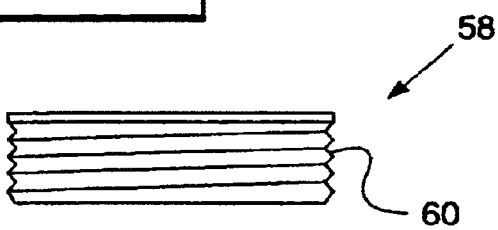
Fig_5_
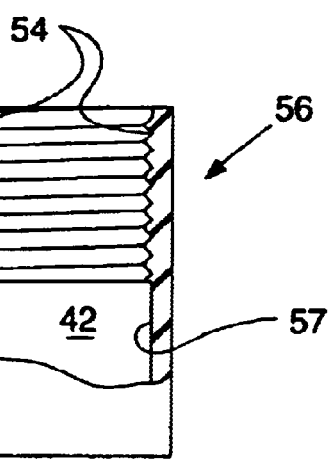
Fig_4_

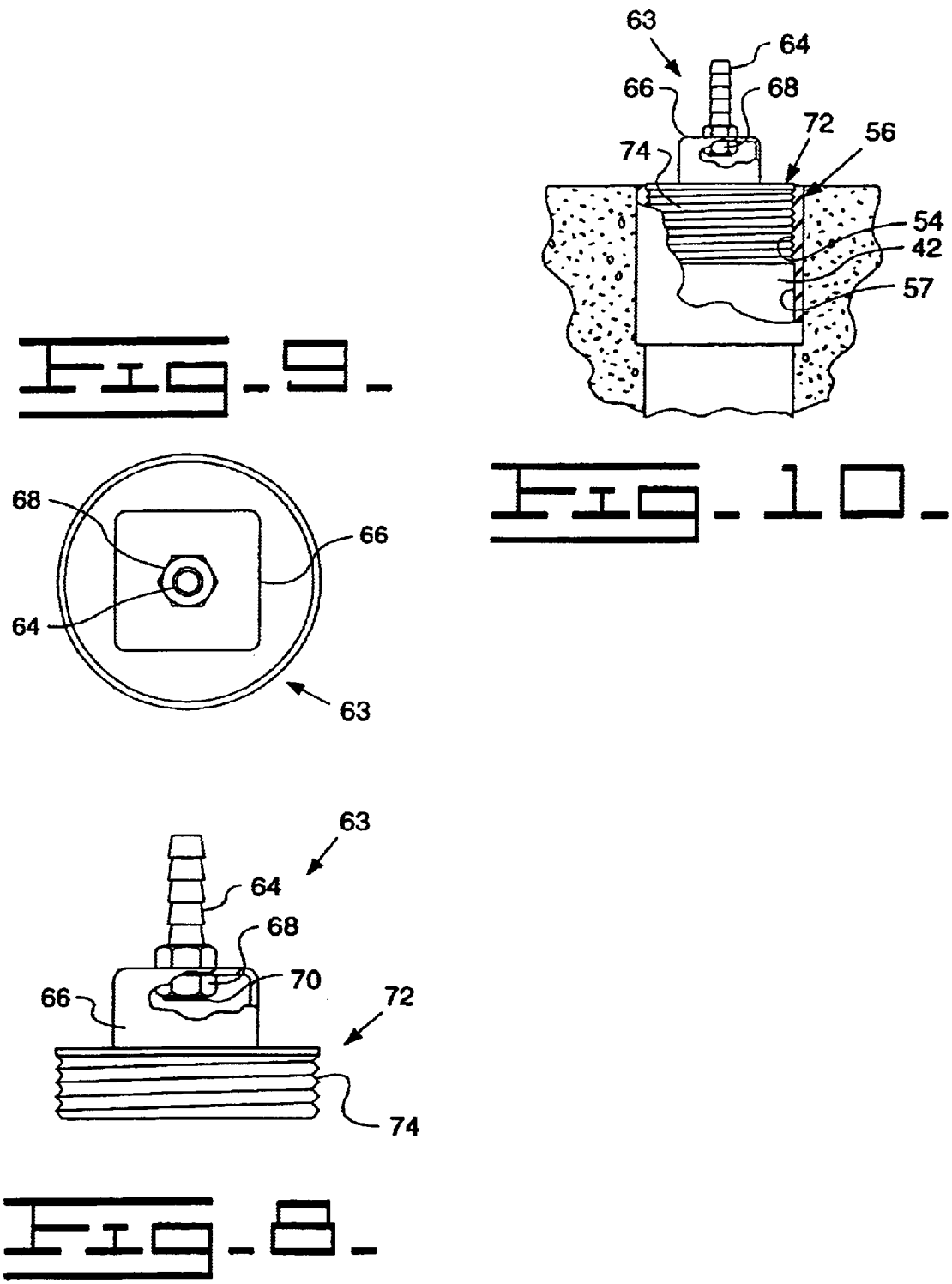

VAPOR TRAP SYSTEM AND ASSOCIATED METHOD FOR DETECTING VOLATILE ORGANIC CHEMICAL VAPORS

BACKGROUND OF THE INVENTION

Although gas and vapor are two terms that are typically used interchangeably, the term "gas" is normally used for substances that exist completely as gases in room temperature. An example of a gas is oxygen. The term "vapor" is more commonly used for substances that generally exist as a liquid or solid at room temperature, although certainly capable of being present in a gaseous phase. Vapor pressure is a physical property of specific materials and is normally measured at a standard temperature of 77° Fahrenheit (25° Celsius). Chemical liquids or other substances that have a vapor pressure greater than the surrounding atmospheric pressure will evaporate into the atmosphere as a vapor and then diffuse outwards until an equilibrium pressure and uniform concentration is reached. Normally, the diffusing vapor (or gas) will reach equilibrium sooner if the volume of the space into which the vapor diffuses is confined or otherwise limited, as in a container, room or beneath a foundation slab. When the available volume into which gases or vapors can diffuse is limited, the resulting vapor pressure and gaseous concentration may reach equilibrium with the evaporating solid or liquid parent material (liquid being the more common of the two types of parent material) and no more material will evaporate. In this situation, the material will exist side-by-side in two different phases. If the available volume into which a gas is diffusing is essentially unlimited, such as the atmosphere itself as found in an uncovered outdoors location, the material will continue to evaporate and diffuse until it is all in the vapor state and the gaseous concentrations are so low as to be difficult to detect. Materials that have a tendency to evaporate at standard temperature and pressure are said to be volatile. If the materials are also organic compounds, they are called volatile organic compounds ("VOCs").

A nonlimiting example of a VOC is perchloroethylene (also known by an assortment of common other names including perc, perchloroethene, tetrachloroethylene, tetrachloroethene, and a variety of trade names), the most widely used chemical in the dry cleaning industry. Perc has a vapor pressure greater than the normal atmospheric pressure of 14.7 p.s.i. at standard temperature and therefore behaves as a VOC and will evaporate. As a liquid, perc has a low interfacial tension and viscosity and readily penetrates into and through typical concrete slab foundations. Once perc has penetrated through a concrete slab into the subsurface beneath, perc begins or continues to evaporate. The accumulating perc vapors do not normally have sufficient pressure to migrate back upwards through the concrete slab (although human exposure to indoor VOC vapors moving upwards through expansion joints, cracks and other penetrations in slabs can become a problem). More often, the perc vapors effectively become trapped below the concrete slab in the pore spaces within the soil. These perc vapors move laterally away from the source area, passing from pore space to pore space within the soil until the vapors become widely diffused in the subsurface beneath the concrete slab. The rate at which the VOC vapors accumulate and migrate depends on the amount of the liquid chemical that has been released, the organic content and the nature of the soil itself and the amount of fluid (normally water) that is also present in conjunction with the VOC or is already residing in the pore spaces.

It is important to detect VOC vapors as close to the source of the release as possible. A basic risk-based closure of facilities that have had a minimal impact or exposure to a VOC, e.g., perc, normally costs tens of thousands of dollars, even without the undertaking of any significant remediation or cleanup effort. Facilities that are significantly impacted, such as perhaps including ground water contamination, easily run into hundreds of thousands of dollars for remediation. This does not include the lost business opportunities, third party liability considerations and other miscellaneous damage claims.

There are a number of systems that monitor the VOC content of the air. Typically, these systems are expensive and difficult to maintain. If the subsurface impacted to the extent the VOC is in the aboveground air in a concentration that is capable of detection, the expense can already be overwhelming in terms of remediation and liability. Examples of this type of technology include that disclosed in U.S. Pat. No. 4,111,034, which issued on Sep. 5, 1978.

The present invention is directed to overcoming one or more of the problems set forth above.

BRIEF SUMMARY OF THE INVENTION

In one aspect of the present invention, a vapor trap for detecting VOCs is disclosed. This system includes a housing, having a first end portion, a second end portion and at least one opening for receiving gas vapor, wherein the housing is at least partially buried in ground and a vapor containment or a vapor sampling mechanism is detachably connected in a fluid relationship to the first end portion of the housing.

In another aspect of the present invention, a method for detecting VOCs utilizing a vapor trap is disclosed. The method includes at least partially burying a housing in ground, wherein the housing includes a first end portion, a second end portion and at least one opening in the housing, wherein the first end portion of the housing is detachably connected in a fluid relationship to a vapor containment or sampling mechanism.

Yet another aspect of the present invention is that VOC releases can be detected before the costs for investigation and clean up become exorbitant.

Still another aspect of the present invention is that VOC releases can be detected before tenants are overwhelmed with inconvenience and expense, which can force the tenant to vacate the premises or property owners to evict the tenant.

Another aspect of the present invention is that VOC releases can be detected before contamination spreads to affect other tenants and property owners to create third party liability.

Yet another aspect of the present invention is that VOC releases can be detected while the contamination is restricted to soil since the contamination of ground water raises the remediation costs and complications significantly.

Another aspect of the present invention is that VOC measurements can be made by technicians without the need of highly specialized, environmental professionals.

Yet another aspect of the present invention is that obtaining VOC measurements on a predetermined basis will demonstrate to an insurance company that the land owner is pro-active about pollution and has the ability to minimize potential problems, which should result in reduced insurance premiums.

Still another aspect of the present invention is that obtaining VOC measurements on a predetermined basis will provide land owners with a mechanism for checking on the general housekeeping practices of a tenant to correct unsatisfactory work practices that can create additional spills and releases of VOCs as well as allowing the land owner to repair leaking equipment.

Another aspect of the present invention is that obtaining VOC measurements on a regular basis provides the tenant with a reminder that the landowner is very serious about preventing pollution.

Yet another aspect of the present invention is that obtaining VOC measurements on a predetermined basis provides evidence that may exonerate either the land owner or the tenant if accused of being a source of a VOC spill or keep either the land owner or the tenant from being falsely blamed as being the cause of unrelated contamination that is either located on-site or off-site.

In another aspect of the present invention is the quick (less than a day), low cost (less than half the price of a regular Phase 1 environmental site assessment) installation with minimal disruption and downtime that can be done with separate self-contained equipment that prevents electrical overload situations at the property where the invention is being installed.

Yet another aspect of the present invention is that very specific constituents in the vapor can be analyzed to minimize false alarms.

Still another aspect of the present invention is that installed vapor traps can be easily removed.

Another aspect of the present invention is that the monitoring of the vapor traps on a predetermined basis can be established through service contracts so that these costs can be budgeted as a regular operating expense.

These are merely some of the innumerable illustrative aspects of this present invention and should not be deemed an all-inclusive listing.

BRIEF DESCRIPTION OF THE DRAWINGS

For a better understanding of the present invention, reference may be made to the accompanying drawings in which:

FIG. 1 illustrates a schematic process diagram of the vapor trap system associated with the present invention;

FIG. 2 illustrates a sectional view of a vapor trap associated with the present invention;

FIG. 3 illustrates a top view of the vapor trap with an installed plug, shown in FIG. 2, associated with the present invention;

FIG. 4 illustrates a side view of a coupling for the vapor trap, shown in FIG. 2, associated with the present invention;

FIG. 5 illustrates a side view of a plug for the vapor trap associated with the present invention;

FIG. 6 illustrates a top view of a plug for the vapor trap, shown in FIG. 5, associated with the present invention;

FIG. 7 illustrates a side view of an installed plug within a coupling attached to a housing, shown in FIGS. 4 and 5, associated with the present invention.

FIG. 8 illustrates a side view of a vapor sampling mechanism associated with the present invention;

FIG. 9 illustrates a top view of the vapor sampling mechanism, shown in FIG. 8, for the vapor trap associated with the present invention;

FIG. 10 illustrates a detailed side view of an installed vapor sampling mechanism including a support structure on a plug cap installed within a coupling attached to a housing, shown in FIGS. 9 and 10, for the vapor trap associated with the present invention.

DETAILED DESCRIPTION OF THE INVENTION

Figure 11:
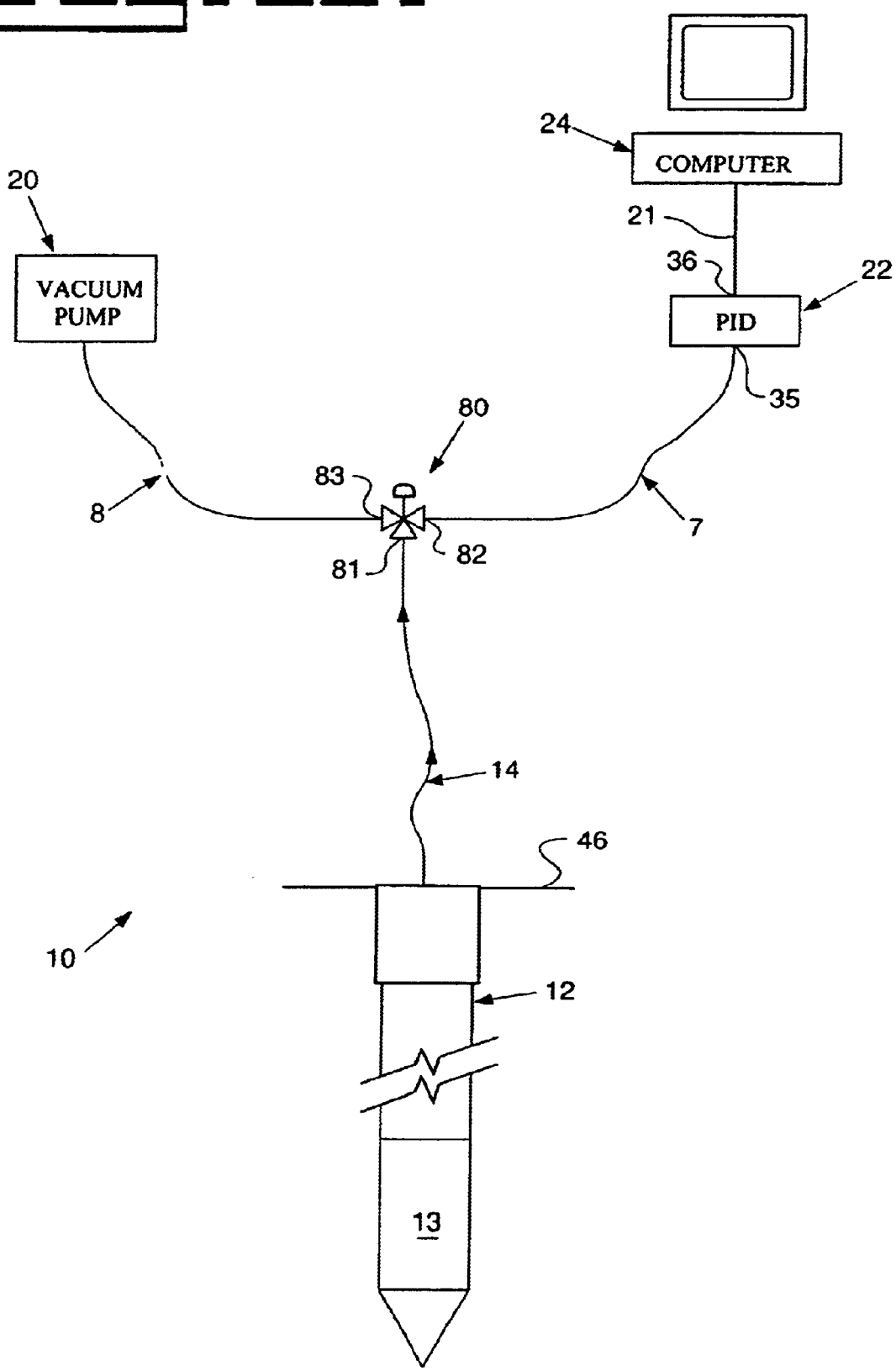
FIG. 11 illustrates a schematic process diagram of an alternative embodiment of the vapor trap system utilizing a three (3) way valve associated with the present invention.

In the following detailed description numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. For example, the invention is not limited in scope to the particular type of industry application, e.g., dry cleaning.

Referring now to the drawings, and initially to FIG. 1, where FIG. 1 is a vapor trap detection system of the present invention, which is generally indicated by numeral 10. This vapor trap detection system 10 of the present invention provides an early warning capability against unknown spills, leaks or other releases of volatile organic compounds ("VOCs") that have somehow reached the ground's shallow subsurface. This particularly includes dry cleaning chemicals, such as perchloroethylene ("perc") as an illustrative, nonlimiting example.

There is a vapor trap for collecting perc and other VOC vapor that is generally indicated by numeral 12. This vapor trap 12 is preferably installed in a strategic shallow subsurface where chemical releases potentially occur. The accumulation of detectable vapors in a below grade trap is a direct indication that a VOC, e.g., perc, is present and generating vapors in the ground's shallow subsurface under a concrete slab 46. The initial presumption would be that a significant release of VOC has occurred at the facility. However, this release may be nothing more than a simple spill that has not been cleaned up. Even though the release occurs during a mere moment in time, the effects can be around for a very long period of time. The presence of a VOC can be detected as early as twelve (12) hours after the release.

As shown in FIG. 1, the preferred embodiment includes tubing 14 extending from and in fluid connection with the vapor trap 12. The tubing 14 is fluidly connected to the bottom inlet 26 of a t-connector 17. A first side outlet 27 of the t-connector 17 is attached in a fluid relationship through tubing 5 to an inlet 30 for a first selector valve 16. The outlet 31 for the first selector valve 16 is connected to tubing 8 that is attached in fluid relationship to a vacuum pump 20. When the first selector valve 16 is open, vapors can be pulled out of the vapor trap 12. A wide variety of commercially available vacuum pumps will suffice in this application, such as that disclosed in U.S. Pat. No. 4,699,570, which issued on Oct. 13, 1987. Although a vacuum pump 20 is preferred, the vacuum pump 20 is not required in utilizing the vapor trap detection system 10 of the present invention.

In addition, the second side outlet 28 of the t-connector 17 is attached in a fluid relationship through tubing 6 to an inlet 32 for a second selector valve 18. The outlet 33 for the second selector valve 18 is connected to tubing 7 that is fluidly attached to an input 35 for an organic vapor analyzer 22. There is an output 36 for the organic vapor analyzer 22 that is electrically connected to a computer 24 through cable 21.

The computer 24 can be a single computer processor or a whole series of computer processors. In addition, any of a wide variety of electronic controllers may suffice.

An organic vapor analyzer 22 is commercially available and disclosed in U.S. Pat. No. 5,563,335, which issued Oct. 8, 1996 and U.S. Pat. No. 5,099,437, which issued on Mar. 24, 1992, which are both incorporated herein by reference. The preferred type of organic vapor analyzer due to the low cost and simplicity of operation is a photo-ionization detector ("PID"). A nonlimiting example of a PID is that disclosed in U.S. Pat. No. 6,225,633, which issued on May 1, 2001, which is incorporated herein by reference.

Referring now to FIG. 2, the vapor trap 12 includes a housing 13 that is preferably in the form of a tube and can be manufactured out of a wide variety of materials. The preferred material for the housing 13 is polyvinyl chloride ("PVC") tubing. Although a wide variety of outer diameters will suffice, a two (2) inch (5.08 centimeters) outer diameter with schedule forty (40) PVC is preferred for most applications. Although the preferred shape is cylindrical, virtually any geometric shape will suffice.

The housing 13 for the vapor trap 12 preferably includes slots 15, screens or some other type of openings to allow for the intake of VOC vapors. The range of distances between the slots 15 can vary extensively with the preferred range between slots 15 being 0.010 inches (0.0254 centimeters) to 0.020 inches (0.0508 centimeters).

The vapor trap 12 is preferably installed into and through the floor of the facility. A preferred, but nonlimiting, distance is approximately two (2) feet (60.96 centimeters) down into the ground 48 underneath the facility. Since perc has been known to penetrate typical concrete slabs 46, which are typically five (5) inches (12.7 centimeters) to six (6) inches (15.24 centimeters) thick found in most commercial establishments, the accumulation of detectable vapors in a below ground vapor trap 12 is a direct indication that a VOC, e.g., perc, is present in the ground 48 and generating vapors in the shallow subsurface. The initial presumption would be that a significant release of perc has occurred at the facility and has been undetected until this point in time.

The vapor trap 12 includes a pointed end cap 40 attached to the bottom of the housing 13 while the top of the housing 13 preferably includes a solid portion 42 that is unslotted.

The vapor trap 12 is preferably installed by coring through the concrete slab 46 with an industrial diamond-tipped coring bit (not shown). The concrete core (not shown) is removed to expose the surface of the ground 48 beneath the concrete slab 46. A cylindrical hole 50 is then dug into the ground 48 beneath the concrete slab 46 using an auger or other means (not shown).

The housing 13 of the vapor trap 12 is then placed into the cylindrical hole 50 and the walls of the cylindrical hole 50 are filled with a porous medium 44 with sufficiently large pore spaces to permit vapor movement up to within a few inches of the surface of the ground 48. A preferred, but nonlimiting, example, of a porous medium 44 includes a transmissive washed pea gravel. The installation is completed by pouring in a sealing material 52 to position the housing 13 in a predetermined location. A preferred, but nonlimiting, example of sealing material 52 is non-shrink concrete grout. Typically, there is a layer of sand 47 located above the ground 48 and below the concrete slab 46.

As shown in FIGS. 2 and 4, a coupling 56, is attached to enclose a top portion of the solid portion 42 of the housing 13. On the top portion, e.g., top half, of the inside of the coupling 56 are internal threads 54 and on the bottom portion, e.g., bottom half, on the inside of the coupling 56 is an unthreaded portion 57. This attachment is between the unthreaded portion 57 of the coupling 56 that preferably encloses the top portion of the solid portion 42 of the housing 13. Attachment is preferably accomplished by the use of adhesives with a low VOC content, although a wide variety of attachment mechanisms will suffice. The coupling 56 can be any of a wide variety of diameters with the preferred inside diameter being two (2) inches (5.08 centimeters). On the inside of the coupling 56 are internal threads 54. This coupling 56 is preferably a standard PVC-type of coupling that has a smooth outer surface.

As shown in FIGS. 3 and 5, there is a plug 58 having external threads 60 on the outside of the circumference of the plug 58 that threadedly interconnects to the internal threads 54 of the coupling 56. The preferred outside diameter of the plug 58 being two (2) inches (5.08 centimeters). The top portion of the plug 58 includes a slot 62, as shown in FIG. 6. This plug 58 is preferably a standard PVC-type of plug.

Referring now to FIG. 7, the plug 58 is installed into the coupling 56 by the interconnection of the internal threads 54 and the external threads 60 where the solid portion 42 of the housing 13 is located inside of the coupling 56.

Referring now to FIGS. 8 and 9, a vapor sampling mechanism 63 is disclosed. This includes a sampling vapor tubing nipple 64 that is attached to a support structure 66. The support structure can be of any geometric shape but is preferably rectangular having a cavity or opening inside. The sampling vapor tubing nipple 64 is secured to the top of the support structure 66 by an optional nut 68 that engages outer threads 70 located on a bottom portion of the sampling vapor tubing nipple 64. However, the preferred structure eliminates the nut 68 and uses a tapered sampling vapor tubing nipple 64 to secure the sampling vapor tubing nipple 64 to the top of the support structure 66. This tapered sampling vapor tubing nipple 64 is tapered from base to tip such that when the tapered sampling vapor tubing nipple 64 is screwed into the support structure 66, the outer threads 70 get tighter and tighter. This tapered fitting for the sampling vapor tubing nipple 64 is airtight and securely fastened without the need for the optional nut 68. The preferred materials for the sampling vapor tubing nipple 64 include both brass and stainless steel.

Referring now to FIG. 10, an installed vapor sampling mechanism 63 is revealed, which includes the sampling vapor tubing nipple 64 that is secured to the top of the support structure 66 by a nut 68. This where the plug 58 has been previously removed from the coupling 56 by an application of a screw driver-type device in the slot 62 of the plug 58, shown in FIG. 6, and applying a counter-clockwise rotation to threadedly disengage the external threads 60 of the plug 58 from the internal threads 54 of the coupling 56. The support structure 66 is fixedly attached to the top of a cap plug 72 or is an integral part thereof. There are external threads 74 on the cap plug 72 that threadedly engage the internal threads 54 of the coupling 56. The preferred outside diameter of the cap plug 72 being two (2) inches (5.08 centimeters).

The installed vapor sampling mechanism 63, which includes the sampling vapor tubing nipple 64, can be formed out of a wide variety of materials. The preferred material can include plastic so that the final installation of the installed vapor sampling mechanism 63 can look like a plastic cap. After measuring a sample with the vapor sampling mechanism 63, the cap plug 72 is threadedly removed from the internal threads 54 of the coupling 56 and is then replaced with the plug 58 where the plug 58 having external threads 60 threadedly interconnects with the internal threads 54 of the coupling 56.

Referring now to FIG. 11, as a first alternative embodiment, the t-connector 17 and the first selector valve 16 and the second selector valve 18 may be replaced by a single three (3)-way valve that is generally indicated by numeral 80. The tubing 14 extending from and in fluid connection with the vapor trap 12 is fluidly connected to the bottom inlet 81 of the three (3)-way valve 80. A first side outlet 83 of the three (3)-way valve 80 is attached in a fluid relationship to the vacuum pump 20 via tubing 8. A second side outlet 82 of the three (3)-way valve 80 is attached in a fluid relationship to the organic vapor analyzer 22, e.g., PID) cell via tubing 7. This operates in the same manner as the previously described preferred embodiment, where both the first side outlet 83 can be selectively opened or closed and the second side outlet 82 can be selectively opened or closed. There is the minor disadvantage of added complexity and expense for the three (3) way valve 80, which can be prone to leakage.

INDUSTRIAL APPLICABILITY

The present invention is advantageously applicable in testing for the presence and nature of VOC vapors. When readings are desired, the plug 58 is threadedly removed from the coupling 56. The cap plug 72, having a support structure 66 with sampling vapor tubing nipple 64, is then threadedly engaged to the coupling 56 through the interaction of the internal threads 54 of the coupling 56 and the external threads 74 of the cap plug 72.

There is tubing 14 attached to the sampling vapor tubing nipple 64, which is shown in FIGS. 8 and 9. The tubing 14 goes from the sampling vapor tubing nipple 64 to the bottom inlet 26 of the t-connector 17. The first side outlet 27 of the t-connector 17 is connected through tubing 5 to an inlet 30 to a first selector valve 16. The outlet 31 of the first selector valve 16 is attached via tubing 8 to a vacuum pump 20, however, for the initial reading, the first selector valve 16 is closed. Gas enters the vapor trap 12 through the bottom inlet 26 of the t-connector 17. The gas enters through the second outlet 28 of the t-connector 17, which is connected to tubing 6 that is attached to an inlet 32 to a second selector valve 18, which is open for the initial reading. Both tubing 5 and 6 are preferably short, e.g., only a few inches or less, to minimize the dead air space between the first side outlet 27 for the t-connector 17 and the inlet 30 for the first selector valve 16 and the dead air space between the second side outlet 28 for the t-connector 17 and the inlet 32 for the second selector valve 18.

The outlet 33 of the second selector valve 18 is attached via tubing 7 to an input 35 for the organic vapor analyzer 22. The preferred type of organic vapor analyzer 22 is a photoionization detector ("PID"). The PID is a field instrument that indicates whether or not airborne VOCs are present. If only air is present (no VOCs) in the vapor trap 12, no reading will be shown on the PID. If VOCs are present, the PID will provide a reading in parts per million ("ppm"). The PID cannot indicate exactly what type of VOC is present, however, a portable gas chromatograph can be used for this purpose. This further identification may be desirable when the VOC in question might be perhaps something other than perc.

There is first an initial reading, which is the result of accumulated vapors collected in the vapor trap 12 over a predetermined time period. A nonlimiting example of a predetermined time period for accumulating vapors is ninety (90) days. This initial reading is due to the fact that the organic vapor analyzer 22 pulls a vacuum and creates a negative pressure drop, which causes soil vapors to move from the pore spaces in the soil (where the pressure is relatively higher than within the vapor trap 12) into the vapor trap 12.

After the initial reading, the first selector valve 16 would be turned off and the second selector valve 18 would be turned on to seal the organic vapor analyzer 22, e.g., PID) cell, and aggressively pull more vapors into the cell from the surrounding ground 48 with the vacuum pump 20. This vacuum from the vacuum pump 20 is much stronger than the vacuum produced by the organic vapor analyzer 22 and would pull vapors from the surrounding soil faster than the vacuum created by the organic vapor analyzer 22, e.g., PID cell, as well as vapors that are relatively further out from the vapor trap 12 than those that can only be drawn in from the vacuum of the organic vapor analyzer 22, e.g., PID cell. Therefore, this secondary reading may provide different values than the initial reading.

After running the vacuum pump 20 for a short period of time, e.g., five (5) minutes, the vacuum pump 20 will be shut-off and the first selector valve 16 will be turned off and the second selector valve 18 will opened and the organic vapor analyzer 22, e.g., PID cell, will be turned back on. As these vapors are pulled in by the lower vacuum of the organic vapor analyzer 22, e.g., PID cell (as opposed to the first reading of the passively accumulated vapors over the predetermined period), readings are taken for this post vacuum period. It has been found that the dead air space between either the first side outlet 27 or the second side outlet 28 to either the first inlet 30 of the first selector valve 16 (when closed) or the first inlet 32 of the second selector valve 18 (when closed) does not affect either the efficiency of either the organic vapor analyzer 22, e.g., PID cell or the vacuum pump 20.

The pre-vacuum and the post-vacuum readings would be compared. These comparisons of either two similar or two different readings, utilized in conjunction with soil and chemical property knowledge along with knowledge of the ultimate disposition and transportation of different substances, e.g., VOCs, in a variety of different media, provide invaluable insight into the potential distance and severity of a heretofore-undetected release of VOCs.

The cost of basic risk-based closures of facilities having minimal perc impact is in the tens of thousands of dollars without performing any actual remediation or clean up. Facilities suffering from significant perc impact, which perhaps involves groundwater, can require hundreds of thousands of dollars of remediation. This does not include lost business opportunities, third-party liability considerations and other miscellaneous damage claims.

This invention need not be limited to dry cleaning establishments only, but can be applied to any building or facility regardless of the commercial or industrial setting. The organic vapor analyzer 22 will simply need to be adapted to respond to a different application.

Other aspects, objects and advantages of the present invention can be obtained from a study of the drawings, the disclosure and the appended claims.

What is claimed is:

1. A method for detecting VOCs in a ground subsurface below a pre-existing floor comprising the steps:

coring through the pre-existing floor to expose the ground subsurface;

digging a hole in the ground subsurface;

installing a vapor trap in said hole, wherein said installed vapor trap has a first end portion above the pre-existing floor and a second end portion is in said hole below the pre-existing floor;

sealing said first end portion of said vapor trap with a removable plug;

removing said removable plug from said first end portion of said vapor trap; and measuring a level of said VOCs in said vapor trap.

2. The method for detecting VOCs as set forth in claim 1, wherein said installing step further comprises the steps of:

placing said first end portion of said vapor trap in said hole;

filling said hole with a porous material around said second end portion of said vapor trap;

securing said vapor trap in said hole; and attaching a coupling to said first end portion of said vapor trap.

3. The method for detecting VOCs as set forth in claim 1, wherein said measuring step further comprises the steps of fluidly connecting an organic vapor analyzer with said first end portion of said vapor trap and pulling VOCs from said vapor trap into said organic vapor analyzer.

4. The method for detecting VOCs as set forth in claim 3, wherein said measuring step further comprises the steps of removably connecting a vapor sampling mechanism with said first end portion of said vapor trap and removably connecting said organic vapor analyzer with said vapor sampling mechanism.

5. The method for detecting VOCs as set forth in claim 3, wherein said measuring step further comprises the steps of fluidly connecting a vacuum pump with said first end portion of said vapor trap and running said vacuum pump.

6. The method for detecting VOCs as set forth in claim 5, further comprising the steps of taking a first set of VOC measurements for accumulated VOCs in said vapor trap before running said vacuum pump and taking a second set of VOC measurements after running said vacuum pump.

7. The method for detecting VOCs as set forth in claim 1, further comprising the step of resealing said first end portion of said vapor trap with said removable plug.

8. The method for detecting VOCs as set forth in claim 7, further comprising the step of servicing a plurality of said vapor traps with said organic vapor analyzer, wherein said organic vapor analyzer is portable.

9. A method for detecting VOCs utilizing a vapor trap comprising:

providing said vapor trap with a partially buried housing in a floor of a building, wherein said partially buried housing comprises an above ground portion and a below ground portion and wherein said vapor trap is sealed with a removable plug;

removing said removable plug from said above ground portion of said vapor trap; measuring a level of said VOCs in said vapor trap; and sealing said above ground portion of said vapor trap with said removable plug.

10. The method for detecting VOCs as set forth in claim 9, wherein said measuring step further comprises the steps of providing a portable organic vapor analyzer, fluidly connecting said portable organic vapor analyzer with said above ground portion of said vapor trap, pulling vapors from said vapor trap into said organic vapor analyzer, and removing said portable organic vapor analyzer from said above ground portion of said vapor trap.

11. The method for detecting VOCs as set forth in claim 10, wherein said step for providing said vapor trap further comprises the steps of coring through a pre-existing floor to expose a ground subsurface, digging a hole in said ground subsurface, installing said vapor trap in said hole, and sealing said first end portion of said vapor trap with said removable plug.

12. The method for detecting VOCs as set forth in claim 10, further comprising the step of servicing a plurality of vapor traps with said organic vapor analyzer.

13. The method for detecting VOCs as set forth in claim 12, wherein said servicing step further comprises the steps of removing removable plugs from said vapor traps, fluidly connecting said organic vapor analyzer with said vapor traps, pulling vapors from said vapor traps into said organic vapor analyzer, removing said organic vapor analyzer from said vapor traps, and sealing said vapor traps with said removable plugs.

14. The method for detecting VOCs as set forth in claim 13, further comprising the steps of fluidly connecting a vacuum pump with said above ground portion of said vapor trap and running said vacuum pump.

15. A method for detecting VOCs utilizing a vapor trap comprising:

at least partially burying a housing in ground, wherein said housing includes a first end portion, a second end portion and at least one opening in said housing;

sealing said first end portion of said housing with a vapor containment mechanism detachably connected thereto; and removing said vapor containment mechanism for measuring a level of said VOCs within said housing.

16. The method for detecting VOCs utilizing a vapor trap, as set forth in claim 15, wherein said step of at least partially burying a housing in ground includes depositing said housing within vapor transmissive material and applying sealing material to position said housing in a predetermined location.

17. A method for detecting VOCs utilizing a vapor trap comprising:

at least partially burying a housing in ground, including depositing said housing in vapor transmissive material and applying sealing material to position said housing in a predetermined location, wherein said housing includes a first end portion, a second end portion and at least one opening in said housing; and fluidly connecting said first end portion of said housing with a vapor sampling mechanism.

18. The method for detecting VOCs utilizing a vapor trap, as set forth in claim 17, wherein said step of at least partially burying said housing in ground includes at least burying said second end portion and said opening and wherein said fluidly connecting step further comprises the step of removing a removable plug from said first end portion.

19. The method for detecting VOCs utilizing a vapor trap, as set forth in claim 17, wherein said burying step further comprises the steps of coring through a floor to expose a ground subsurface;

digging a hole in said exposed ground subsurface; and installing said housing in said hole, wherein said first end portion remains above said floor and said second end portion is in said cylindrical hole below said floor.

20. The method for detecting VOCs utilizing a vapor trap, as set forth in claim 17, wherein said at least one opening of said vapor trap includes a slot.

21. The method for detecting VOCs utilizing a vapor trap, as set forth in claim 17, further includes utilizing an organic vapor analyzer that is fluidly connected to said vapor sampling mechanism.

22. The method for detecting VOCs utilizing a vapor trap, as set forth in claim 21, further includes utilizing a vacuum pump that is fluidly connected to said vapor sampling mechanism for applying a vacuum to draw vapors into said organic vapor analyzer.

23. The method for detecting VOCs utilizing a vapor trap, as set forth in claim 22, further includes a first selector valve located between said vapor sampling mechanism and said vacuum pump and a second selector valve located between said vapor sampling mechanism and said organic vapor analyzer.

24. A method for detecting VOCs utilizing a vapor trap comprising:
- at least partially burying a housing in ground, wherein said housing includes a first end portion, a second end portion and at least one opening in said housing;
- sealing said first end portion of said housing with a vapor containment mechanism detachably connected thereto;
- removing said vapor containment mechanism; and
- fluidly connecting said first end portion of said housing with a vapor sampling mechanism and measuring an amount of VOCs present in said housing with an organic vapor analyzer fluidly connected to said vapor-sampling mechanism.

25. The method for detecting VOCs utilizing a vapor trap, as set forth in claim 24, further comprising the steps of removing said organic vapor analyzer from said vapor-sampling mechanism, resealing said first end portion of said housing with said vapor containment mechanism, and servicing a plurality of vapor traps with said organic vapor analyzer.

* * * * *